Nov. 17, 1970 H. A. JOHNSON, JR., ET AL Plant Pat. 3,001
STRAWBERRY PLANT
Filed Oct. 15, 1968
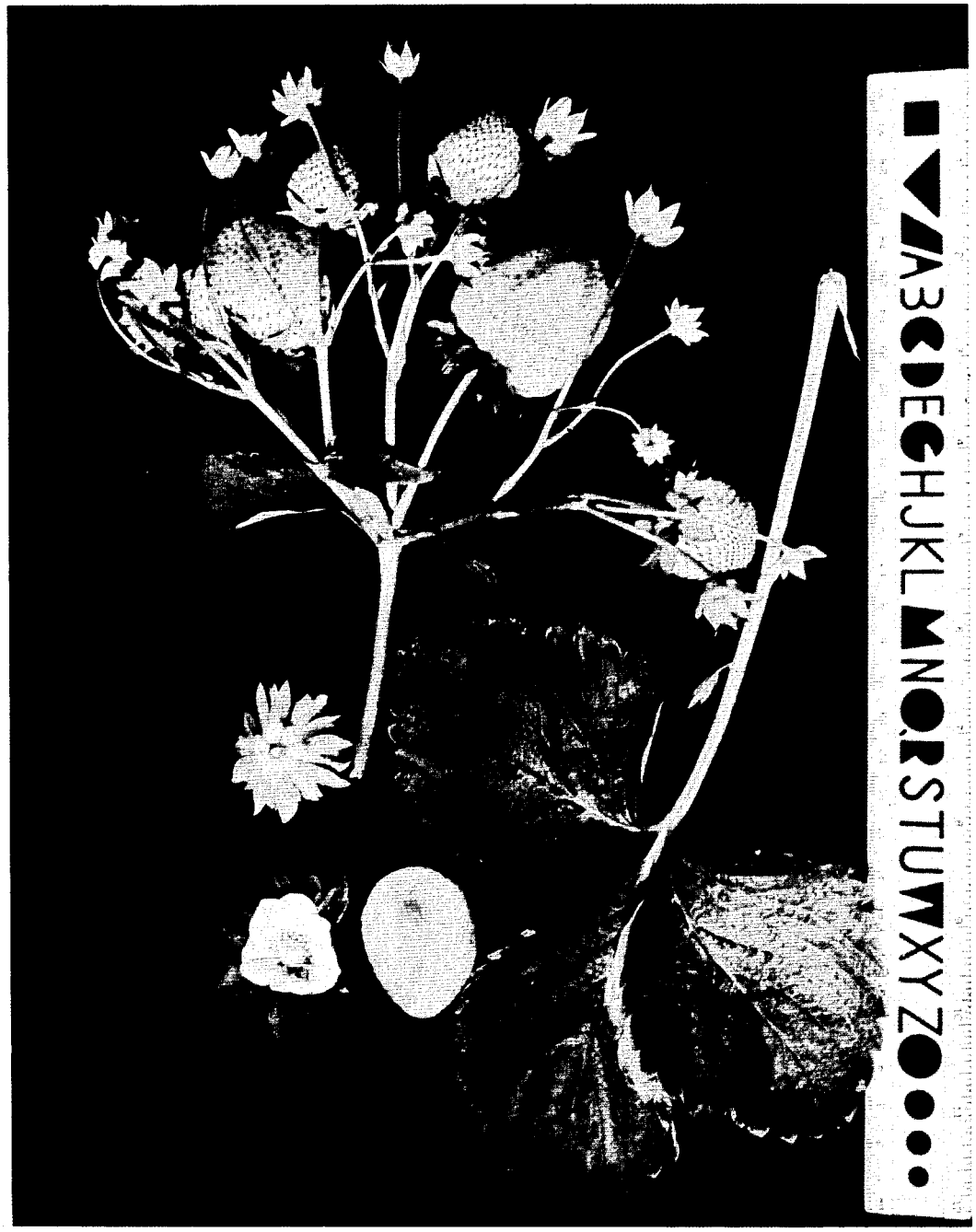
INVENTORS.
HAROLD A. JOHNSON, JR.
HAROLD E. THOMAS
BY Townsend and Townsend
ATTORNEYS United States Patent Office Plant Pat. 3,001
Patented Nov. 17, 1970

3,001
STRAWBERRY PLANT

Harold A. Johnson, Jr., and Harold E. Thomas, Watsonville, Calif., assignors to Driscoll Strawberry Associates, Inc., Watsonville, Calif.

Filed Oct. 15, 1968, Ser. No. 767,858
Int. Cl. A01h 5/03
U.S. Cl. Plt.—49 1 Claim This invention relates to a new and distinct variety of strawberry plant which is the result of a cross of the unpatented everbearing variety known as The Strawberry Institute of California selection No. L88.101 and Goldsmith Pat. No. 1,735 issued July 29, 1958.

The seedlings resulting from the aforementioned cross were grown and asexually multiplied in Shasta County, Calif.; and tested in the fruiting beds on the property of growers of the Driscoll Strawberry Associates, Inc. Clones of these seedlings were also held at the Propagation Nursery in Shasta County. One plant was selected from the aforementioned group of seedlings, and further asexual reproduction was performed in the Shasta County nursery of Driscoll Strawberry Associates, Inc. Tests followed in various parts of California during intervening seasons on various properties of grower members of the Driscoll Strawberry Associates, Inc. These tests indicated the merit of this new plant and resulted in its selection as a promising test variety.

Parts of a plant of the new variety, typical in size, shape and color are pictured in the accompanying drawing in which two ripe berries are shown. To exemplify flesh color and core cavity, a third berry is shown in cross section. The inflorescence pictured is typical of branching and relative size on or about the middle of July during which the leaf shown is also typical in appearance and size. The flower shown is a typical primary but not unlike secondaries.

The plant is of medium size but vigorous. It is an everbearing variety in that it may be planted during the spring as well as winter and a crop can still be realized the same growing year. This variety is slower to come into production than many of the everbearers used by Driscoll Strawberry Associates, Inc. but will crop until late fall. Primary and secondary fruit produced by this variety is medium to good in size especially during the early periods of production. Subsequent production produces fruit that is not as large but is still acceptable for fresh fruit shipments.

Characters which distinguish this new variety are its flower, fruit and plant characteristics. A planting of this new variety is conspicuous because of the large white flowers that appear above the foliage. Many primary flowers have six to eight petals. The flower petals which are folded and cupped upward give the flowers a conspicuous appearance. The anthers produce an abundance of pollen giving this variety the ability to produce well shaped fruit, even under cold, wet, windy conditions. Inflorescences may produce several open flowers at one time. The irregularity of the fruit shape is a distinguishing character. Most fruit is irregularly short wedge as described in the U.S.D.A. Bulletin No. 1043. Most berries are only slightly longer than wide. The early produced fruit as large as the Institute E2 variety. (The Institute E2 is an everbearing variety, U.S. Pat. No. 2,611.) Subsequent production produces fruit not as large as the E2, but more fruit at one time during the peak of its production. The fruit is also lighter in color than E2. The fruit surface is smoother than the E2, even though the general shape is more irregular. If mildew is not controlled, it may be present on the fruit as well as foliage, giving the berries a mottled appearance. The fruit is darker in flesh color than the E2, and has a larger cavity.

The dessert quality of this berry is medium and distinct in that it has a strong acid taste with low sugar. The seeds of this new variety are medium in size and evenly spaced on the surface of the fruit usually being held even to slightly exserted above the surface. The fruit often produces some longitudinal ribbing and the apex of the wedge shaped fruit may often produce multiple blunt tips.

The berries of this new variety produce skin firm enough for commercial shipments to eastern markets. The skin and flesh are both considered as firm as E2 during most of the picking season. It may be weaker during summer periods. The inflorescence of the new variety is medium in length and is generally equal to that of E2. The pedicel holding primary berries of most inflorescences originates from the axial formed by the union of peduncles, but occasionally originates from one of the peduncles. The inflorescence may produce a primary and a secondary fruit ripening at the same time. Large bracts are often produced at the main axil of the peduncles. Some inflorescences often produce pedicles holding tertiary berries that are fused together.

The calyx is large and conspicuous, with those of the primary berries generally large, having more sepals than E2. There is considerable overlap of sepals with an elliptical sepal generally overlapping a multiple tipped sepal as is demonstrated in the accompanying drawing. Most calyxes are held in a reflexed position. The plant of this new variety is equal in size to the E2, but usually becomes denser with more vigor during the fall period. The average total leaf length, including the petiole, is equal to or slightly longer than the E2. The plant is lighter in color than the E2, especially early in the growing season. Individual leaflets are not as large as those of E2 and have a length slightly larger than the width. The leaflets of this invention are cupped upward and are not as thick as the E2. This new variety has an abundance of hair on the upper side of the leaflets, noticeably more than the E2 variety. Bracts are often present growing on the petioles. The natural leaf cupping of this new variety is often increased by the presence of mildew. The plant is susceptible to verticillium wilt, red stele, powdery mildew and the two-spotted mite. As a seedling, this variety withstood the natural virus invasion of the virus components found in the Watsonville area of central California without losing its ability to produce. There is generally no particular aroma peculiar to the flesh of this variety. At the nursery this new variety is considered a medium to good runner maker and produces more runner plants than the E2 variety.

The varietal characteristics of this new plant, described below in detail, were observed during the first fruiting season. Observations were made in the Watsonville area of California which is a cool coastal area near the Pacific Ocean. The color terminology is in accordance with Ridgway's Color Standards and Nomenclature (1912 Edition).

*Plant.*—Medium in size, slightly dense at times, with a medium root system.

*Leaves.*—Medium to large in size. The central leaflet is mostly 6 to 8 cm. in diameter. The length is slightly greater than the width. Leaflets are moderately rugous with many serrations per leaflet. The serrations at the margin are ovate with an acute apex becoming noticeably pointed, often becoming double pointed. Petioles are medium to long in length with bracts often present. The pubescence on upper side of leaflets is noticeably abundant. The leaflet upper side color at Watsonville in July is Forest Green, Plate XVII.

*Runners.*—Abundant, vigorous at the nursery but may be scarce in the fruiting bed.

*Inflorescence.*—Medium in length, often producing two or more ripe berries at one time on each inflorescence. The pedicel holding the primary berry usually originates from the axil formed by the union of peduncles. The pedicels holding tertiary fruit are often fused together. Flowers have anthers that produce an abundance of pollen even under cold, wet, windy conditions. Flowers are conspicuously visible above the plant and produce 5 to 8 petals per flower with primaries up to 30 to 40 mm. in diameter. Petals are often folded lengthwise and directed upward.

*Fruit.*—Large, dropping in size during the season. Primary berries during July average 35 to 45 mm. in length as well as width. Fruit shape varies considerably, but mostly short wedge in shape as described in the U.S.D.A. Bulletin No. 1043. The shoulders of most berries are large and round, not necked. The fruit surface is mostly smooth, firm and light in color, with a medium high gloss. Some longitudinal ribbing may be present. Both the surface and flesh color are Scarlet Red, Plate I.

*Seeds.*—Abundant and evenly spaced, medium in size very few are non-fertile. The seeds are held mostly even with the fruit surface. The color is Apricot Yellow, Plate IV, becoming darker when exposed to full sunlight.

*Calyx.*—Large; the calyx of most primary berries is 35 to 40 mm. The sepals are large and abundant, generally overlapping each other and becoming deeply serrated at the apex. The calyx is capped from the fruit with difficulty except when fruit is completely ripe. The sepal color on the side facing the fruit is Light Elm Green, Plate XVII.

We claim:

1. The new and distinct variety of strawberry plant herein described and illustrated, and identified by the characteristics enumerated above.

No references cited.

ROBERT E. BAGWILL, Primary Examiner